United States Patent [19]

Pertchik

[11] 4,255,824
[45] Mar. 17, 1981

[54] CUSHION FOR DECUBITUS ULCERS

[76] Inventor: Samuel Pertchik, 225 E. Beech St., Long Beach, N.Y. 11561

[21] Appl. No.: 46,476

[22] Filed: Jun. 7, 1979

[51] Int. Cl.³ .............................................. A47G 9/00
[52] U.S. Cl. .......................................... 5/441; 5/442; 5/449; 5/458; 297/456
[58] Field of Search .................... 297/456; 5/441, 442, 5/449, 451, 458

[56] References Cited

U.S. PATENT DOCUMENTS

| | | | |
|---|---|---|---|
| 1,361,453 | 12/1920 | Frey | 5/449 |
| 2,239,300 | 4/1941 | O'Dell et al. | 5/449 |
| 2,843,181 | 7/1958 | Paschen | 5/441 |
| 3,602,928 | 9/1971 | Helzer | 5/441 |
| 3,965,508 | 6/1976 | Hunter | 5/451 |
| 4,115,885 | 9/1978 | Davis | 5/451 |

Primary Examiner—Casmir A. Nunberg
Attorney, Agent, or Firm—McAulay, Fields, Fisher, Goldstein & Nissen

[57] ABSTRACT

A cushion for the relief of, and the prevention of Decubitus Ulcers, has two elongated cylindrical portions spaced apart from each other over a substantial portion of their length, and supported in substantially the same plane by two similar cylindrical portions. The cylindrical portions are inflatable sealed cylinders which have interconnecting openings whereby inflation of all of the cylinders is accomplished through a single valve in communication with one of the cylinders. The cylinders may be inflated by any of a number of fluid media including air and other similar gaseous materials; foam, mud, or any other similar liquid materials.

5 Claims, 6 Drawing Figures

CUSHION FOR DECUBITUS ULCERS

BACKGROUND OF THE INVENTION

Decubitus Ulcers, the most common example of which are so-called bed sores, are ulcers or blisters which form on the skin of a person who is constrained to sit or lie in a fixed position for long periods of time. This is most usually a problem with persons who are temporarily disabled, such as persons forced to lie in a fixed position in a hospital bed because they are unable to move themselves. It is also a problem with persons who are permanently disabled and may be without "feeling" in the lower portion of their body. The latter case is quite serious as these people are unaware of the formation of the ulcers and therefore do not ask to be moved when attendants are not themselves alert to the problem. Serious cases of Decubitus Ulcers can require corrective surgery.

To avoid the formation of the ulcers, and in minor cases to effect reversal of the condition, a patient is normally rolled, if bedridden, or moved in various positions if constrained to sit. This prevents constant irritation on the same spots. Various cushions have also been utilized to spread the pressure of sitting in one position, both to avoid the formation of the ulcers and as a treatment of them by reducing further iritation. Unfortunately, the known cushions suffer from a number of disadvantages One type of cushion is commonly known as a "doughnut." As the name implies, the doughnut is an inflated circular or doughnut shaped cushion, not unlike a small tire tube. This spreads the pressure somewhat. However, in practice, the doughnut does not sufficiently spread the pressure but rather transfers it to a circular region in contact therewith. It is possible that extended use of the doughnut will itself cause ulcers to form. Moving the patient about on the doughnut to avoid having the pressure occur at the same places has been found dangerous especially for patients that are partially paralyzed. Moving the patient more then a little off-center can cause the patient to tip over and fall, especially where the patient is physically unable to regain equilibrium as is often the case.

A cushion known as a "lamb skin" is somewhat better than the doughnut in that it spreads the pressure more evenly over a larger area. Basically the lamb skin appears to be similar to the fur on a piece of lamb skin but is anchored in a softly woven support. It is somewhat like a woven lamb skin carpet or the like. Although somewhat better than a doughnut, the lamb skin suffers from some of the same problems in that pressure areas will develop from a matting down of the cushion, resulting again in the formation of new ulcers although in different places.

About the best of the presently available prior art cushions are the water cushions. These are cushions filled with water. Water cushions have been found to do a better job of spreading the pressure but the patient is still cradled in contact with the cushion. Ulcers formed on the patient will therefor necessarily be in contact with a part of the cushion although the pressure will be lessened.

It is an important object of the present invention to provide a cushion for the prevention or alleviation of Decubitus Ulcers.

BRIEF DESCRIPTION OF THE DISCLOSURE

Briefly, the preferred embodiment of the Decubitus Ulcer cushion, according to the present invention, comprises two cylindrical portions disposed substantially in the same plane and two additional cylindrical portions disposed substantially in a second plane and on top of the first two cylindrical portions. The cylindrical portions are in the form of inflatable cylinders.

The cylinders are configured in a tic-tac-toe board form in two planes wherein the cylinders in each pair are substantially parallel to each other and at right angles to the cylinders in the other pair.

The cushions must be spaced apart from each other at least substantially along their lengths in order to provide a stable support for the person using the cushion. The preferred tic-tac-toe board configuration, having its two lower cushions spaced apart from each other and parallel to each other, is particularly stable. The upper two cushions are positioned against a portion of the patient which does not have ulcers formed thereon. This provides support for the patient without applying pressure to the ulcers. The cushion may also be rotated to various positions with respect to the patient thereby to prevent the formation of ulcers as a result of contact with the cushion. The configuration of the cylinders forms a stable platform for the patient irrespective of the way in which the cushion is rotated.

By interconnecting the cushions with openings therebetween at the interstices of the cushions, it is possible to use only one valve to fill all of the cushions. The inflating media may be any gaseous or liquid substance, most preferably either air, water or a foam or foaming material.

The cushions need not be parallel to each other for the operation of the device and, in fact, it may be found to be convenient to have at least one pair of the cushions intersect. Thus, the upper cushions can be in the form of a "V" with or without fluid communication at the apex of the "V." This may be a manufacturing convenience, depending on the manner in which the device is made, as it allows one long cushion to be bent into two cushions.

The tubes need not be interconnected but may be separately inflatable. It is only necessary that they be secured together to form a stable cushion irrespective of how it is positioned.

DESCRIPTION OF THE PREFERRED EMBODIMENT

Figure 1:
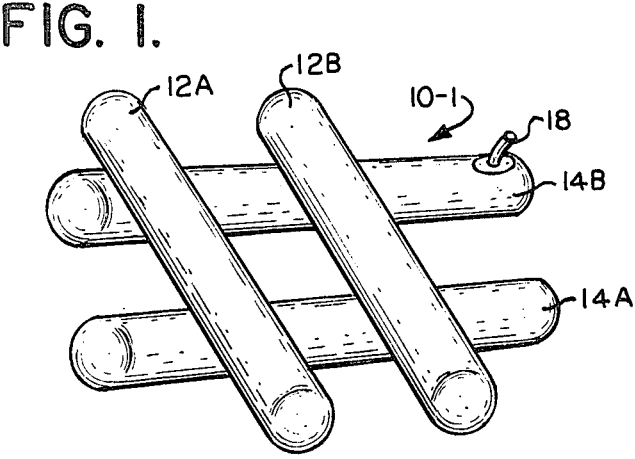
FIG. 1 shows a Decubitus Ulcer cushion in the "tic-tac-toe" configuration.

With reference to FIG. 1, a Decubitus Ulcer cushion 10-1 is formed of upper support cushions 12A, 12B, and lower stabilizing cushions 14A, 14B.

In the embodiment of FIG. 1, the stabilizing (lower) cylinders 14A, 14B, hold the (upper) support cylinders 12A, 12B in spaced apart relationship with respect to each other and in spaced apart relation from the support surface on which the patient is to sit or lie. This arrangement puts the support of most of the weight of the patient on support cylinders 12A, 12B, while the lower stabilizing cylinders 14A, 14B restrain contact of the patient with the surface on which the patient is to sit or lie.

Figure 2:
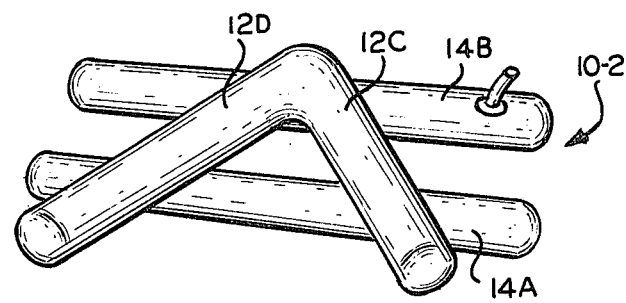
FIG. 2 shows a Decubitus Ulcer cushion with upper cylinders in the "V" configuration.
Figure 3:
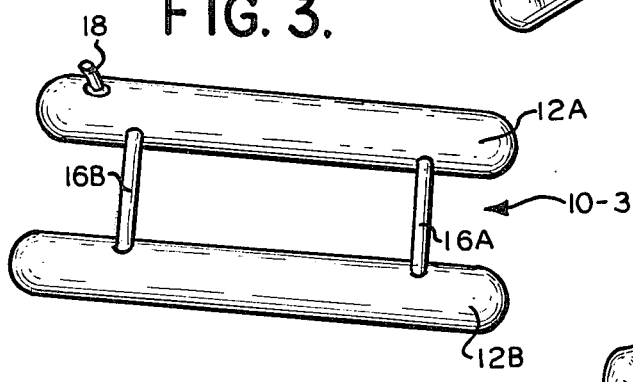
FIG. 3 is a Decubitus Ulcer cushion similar to the cushion shown in FIG. 1 but with the lower cylinders replaced by interconnecting tubing.

In the modification shown in FIG. 3, upper support cylinders 12A, 12B are supported in spaced apart relationship by interconnecting means 16A, 16B. Preferably, these interconnecting means comprise conduits whereby cushions 12A, 12B may be in fluid communication with each other. This normally results in a cushion which is lower than the cushions of FIGS. 1 and 2 thereby making it more comfortable for use in the reclining position.

Figure 5:
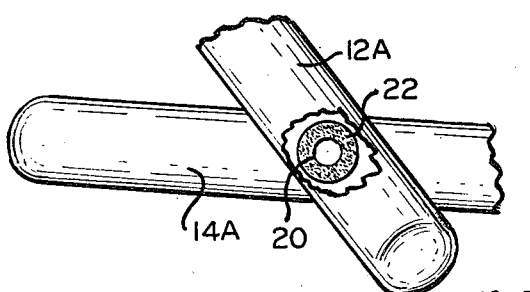
FIG. 5 shows a detail of the interconnection between cylinders.

Cylinders 12A-12F are inflatable cylinders which may be inflated with any suitable fluid media. Air and water are two possible media which have been found useful for this purpose. Foaming agents may be used in the cushions in conjunction with water. Other materials may be admixed with the water to alter its physical characteristics. Thus, mud or gel may also be used. By intercommunicating the various cylinders with each other, a single inflation valve 18 can be used to inflate all of the cylinders at one time and from a single source. As shown in the detail of the embodiment illustrated in FIG. 5 with a portion of cylinder 12A torn away, the interconnection 20 between the cylinders 12A, 14A is preferably in the form of a coextensive opening 20 formed at the interstice of the cylinders 12A, 14A in the area of reinforced heat seal 22 whereby the cylinder 12A, 14A are secured together. Similar interconnections may, of course, be used between any two cylinders forming the Decubitus Ulcer cushion of the present invention.

In the embodiment of FIG. 3, upper support cylinders 12A, 12B are secured together by interconnecting means 16A, 16B which may comprise fluid conduits. When either interconnecting means 16A, 16B forms a fluid conduit to interconnect support cylinder 12A, 12B, only one inflation valve 18 is required. However, if the interconnecting means 16 do not include fluid conduits, separate inflation valves 18, 18 will need to be provided for each support cylinder 12A, 12B. This is illustrated in FIG. 6 wherein interconnecting means 16C, 16D are provided in the form of adjustable straps whereby the spacing between support cylinders 12E, 12F may be conveniently adjusted.

Figure 4:
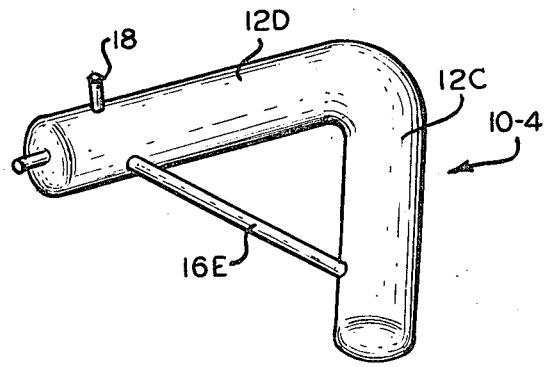
FIG. 4 is a Decubitus Ulcer cushion similar to the cushion of FIG. 2 wherein one of the parallel cylinders has been eliminated and the other has been replaced with an interconnecting tube or strap.
Figure 6:
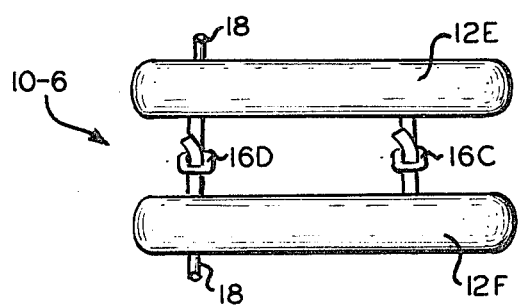
FIG. 6 is a Decubitus Ulcer cushion similar to the cushion of FIG. 3, showing adjustable length interconnecting means between the cylinders.

The Decubitus Ulcer cushions 10-2 and 10-4 of FIGS. 2 and 4 are generally similar to the cushions 10-1, 10-3, 10-6 shown in FIGS. 1, 3 and 6 except that the arrangement of the upper support cylinders 12C, 12D is in a "V" type configuration. As shown in FIGS. 2 and 4, the cylinders 12C, 12D intersect each other at one end. This reinforces and stabilizes the spaced apart relationship between the upper support cushions 12C, 12D. However, as is evident from the embodiment of FIG. 1 and of FIG. 3, intersection of the upper cushions 12C, 12D is unnecessary and they may just be in generally parallel or non-parallel spaced apart relation.

The Decubitus Ulcer cushion 1-4 shown in FIG. 4 bears the same relationship to the Decubitus Ulcer cushion of FIG. 2 as does the Decubitus Ulcer cushion of FIG. 3 to the Decubitus Ulcer cushion of FIG. 1. An interconnecting means 16E secures the opened end of the "V" shape together. A second interconnecting means is unnecessary where the support cylinders 12C, 12D interconnect. Interconnect means 16E may be adjustable analogously with the device shown in FIG. 6 or may be fixed. If either the interconnect means 16E or the intersection of the cylinders 12C, 12D includes a fluid conduit or interconnection means, only one valve 18 need be provided. Otherwise a separate valve for each cylinder 12C, 12D will be required.

The methods for manufacturing a Decubitus Ulcer cushion in accordance with the present invention are generally well-know. It is preferred that the cushions be made of flexible material, preferably rubber or synthetic polymers which may be welded or otherwise secured to form the various shapes and forms, and to interconnect and seal together the various elements which comprise the Decubitus Ulcer cushion. Polyvinylchloride or "vinyl" is one well-known material for which the necessary technology to fabricate a Decubitus Ulcer cushion according to the present invention is readily available. Rubber, as is usually employed for prior art "doughnut" cushions, is another material for which technology necessary for fabrication, is readily available.

The valve 18 may be a simple check valve such as is often employed in automobile tires, especially if air is to be used. The valve 18 may also be a simple tube which can be closed after inflation. This second type of valve is useful if water or other liquid is to be used to inflate the device.

The above is by way of illustration of presently preferred embodiments of the invention and not intended as limitations on the scope of the invention, as other modifications and embodiments would be obvious to a skilled worker in the art. Thus, for example, although the Decubitus Ulcer cushion shown in FIG. 2 has the "V" shaped cylinder arrangement for the upper support cylinders, a comparison of FIGS. 1 and 2 would lead one to realize that the cushion can be inverted and the cylinders presently indicated as the lower stabilizing cushions 14A, 14B can, in fact, operate as the upper support cylinders. The advantage of such an arrangement is that, in use, this allows additional possibilities for the placement of the cylinders against the body of the patient thereby providing still further adjustment to prevent Decubitus Ulcers. In addition, although the various cylinders which comprise the Decubitus Ulcer cushion are illustrated in FIGS. 1 and 2 as being substantially the same size, clearly from the embodiments of FIGS. 3 and 4, the relative sizes of the cushions can be altered. Where smaller or no lower cylinders are used, the size of the upper cylinders can be increased, depending on the inflation medium, and the weight of the patient, to meet particular requirements. A series of differently sized cushions can also be made to accommodate differently weighted and sized patients, as required. By using adjusting straps as shown in FIG. 6, a single embodiment can be used for a number of differently sized and weighted patients by adjusting the space between the cylinders 12A, 12B and the inflation pressure thereof.

Therefore, the scope of the invention should be measured only as set forth in the Claims.

What is claimed is:

1. A Decubitus Ulcer cushion for alleviation or prevention of the formation of decubitus ulcers in immobile patients comprising:

first and second inflatable substantially cylindrical support cylinders defining a first plane and being disposed in spaced apart relation with respect to each other with at least one pair of corresponding end portions separated to form an open-ended cushion; and interconnecting means defining a second plane and securing said support cylinders to each other to restrain separation between said first and second support cylinders beyond a predetermined maximum extent.

2. The Decubitus Ulcer cushion of claim 1 wherein said interconnecting means comprises two inflatable lower stabilizing cylinders, and said second plane being disposed below said first plane to raise the support cylinders for better patient support.

3. The Decubitus Ulcer cushion of claim 1 wherein said upper support cylinders are in substantially parallel relation with respect to each other and said interconnecting means comprises third and fourth inflatable cylindrical cylinders substantially parallel with respect to each other and intersecting said first and second inflatable cylindrical cylinders at substantially right angles to form a tic-tac-toe board arrangement.

4. The Decubitus Ulcer cushion of claim 1 wherein said first and second support cylinders are non-parallel with respect to each other and intersect at one end;

said interconnecting means comprising an elongated connector securing portions of said intersecting cylinders together at portions spaced apart from the intersection thereof.

5. The Decubitus Ulcer cushion of claim 1 wherein said interconnecting means comprises an adjustable strap.

* * * * *